United States Patent
Gergely et al.

(10) Patent No.: US 6,932,979 B2
(45) Date of Patent: Aug. 23, 2005

(54) SOLUBLE, GUM-CONTAINING, COATED CHEWABLE TABLET

(75) Inventors: Gerhard Gergely, Vienna (AT); Irmgard Gergely, Vienna (AT); Thomas Gergely, Vienna (AT)

(73) Assignee: Dr. Gergely & Co., Vienna (AT)

( * ) Notice: Subject to any disclaimer, the term of this patent is extended or adjusted under 35 U.S.C. 154(b) by 0 days.

(21) Appl. No.: 10/407,134

(22) Filed: Apr. 7, 2003

(65) Prior Publication Data

US 2003/0206948 A1 Nov. 6, 2003

Related U.S. Application Data

(63) Continuation of application No. 09/479,224, filed on Jan. 7, 2000, now abandoned, which is a continuation-in-part of application No. PCT/EP98/03306, filed on Jun. 3, 1998.

(30) Foreign Application Priority Data

Jul. 10, 1997 (EP) .............................................. 97111783

(51) Int. Cl.$^7$ ................................................. A61K 9/20
(52) U.S. Cl. ...................... 424/441; 424/465; 424/484; 424/439
(58) Field of Search ................................ 424/441, 465, 424/464, 484, 439, 440

(56) References Cited

U.S. PATENT DOCUMENTS

| | | | | |
|---|---|---|---|---|
| 4,753,800 A | * | 6/1988 | Mozda | 424/440 |
| 5,637,313 A | * | 6/1997 | Chau et al. | 424/440 |
| 5,648,092 A | * | 7/1997 | Weckenmann et al. | 424/464 |

FOREIGN PATENT DOCUMENTS

| | | |
|---|---|---|
| EP | 212641 | 3/1987 |
| GB | 1538280 | 1/1979 |
| WO | 8603967 | 7/1986 |

OTHER PUBLICATIONS

The Merck Index (Merck & Co., Inc 1983) p. 4243.*
International Search Report.
Derwent Publications Ltd.—XP 002049401 (Abstract).

* cited by examiner

Primary Examiner—James M. Spear
(74) Attorney, Agent, or Firm—Rothwell, Figg, Ernst & Manbeck, PC

(57) ABSTRACT

The soluble, rubber-containing, coated chewable tablet contains chewable components, syrup components and fat or wax components and optionally fillers. It can be prepared by a process in which pulverulent chewable components are mixed with the molten fat or wax components. The mixture, with the addition of at least one syrup component, then becomes a crumbly material, which is then cooled to below 0° C., then milled to a particle size of not more than 5 mm and, after cooling to below 10° C., compressed to give tablets which are coated in a known manner. The finished product—due to compression of the cooled granules—presumably has a partially granular structure in which the moisture has been initially immobilized by the low temperature. After compression, this moisture becomes mobile as a result of heating (in particular during the coating process) and migrates or diffuses—initially at the surface—into the water-soluble ingredients present. These are partially dissolved and give a highly viscous, thixotropic, chewable material.

31 Claims, No Drawings

SOLUBLE, GUM-CONTAINING, COATED CHEWABLE TABLET

CROSS-REFERENCE TO RELATED APPLICATIONS

The present application is a continuation of application Ser. No. 09/479,224, filed on Jan. 7, 2000, now abandoned which is a continuation-in-part of International Application No. PCT/EP98/03306, filed on Jun. 3, 1998.

Chewing gum formulations based on natural rubber have been widely used in the pharmaceutical industry. Their advantages are the pleasant and popular dosage form and rapid, sublingual absorption of an active ingredient. However, the serious disadvantage of such formulations is a rubber material which remains after chewing and which has resulted in, for example, antiemetics based on this material being undesired in aircraft and, for example, simply the possession of chewing gum being punishable in Singapore.

On the other hand, it is also known from the confectionery industry that gum arabic and sugar-containing solutions can be boiled and can be cast in suitable shapes which are then optionally coated. For example, the two U.S. Pat. Nos. 4,698,232 and 5,476,678 describe fiber-containing chewable materials having a foamed matrix of gum arabic and gelatin and an unfoamed matrix of sugar syrup.

DE-A1-4444051 describes a chewable tablet which rapidly disintegrates in the mouth and in which hydrophilic active ingredient particles are coated with or embedded in a hydrophobic material, optionally with or in gum arabic. GB-B-1142377 describes a chewable tablet for cleaning the teeth, in which one part each of gum arabic and gelatin are mixed with two parts of glycerol and various small amounts of additives.

For the preparation of a pharmaceutical formulation, all these products and their production processes are unsuitable or only of limited suitability. On the one hand, it is desired to achieve slow release to the body distributed over several minutes in the case of various active ingredients, e.g. antiemetics or disinfectants; the formulation ideal to date for this purpose, in a chewing gum, is increasingly meeting resistance, as already mentioned. On the other hand, the production process known from the confectionery industry often cannot be used for the high requirements of good manufacturing practice in the pharmaceutical industry and is much too expensive for relatively small batches, also in terms of the cost of the apparatus.

It is therefore the object of the invention to provide a composition and a process in which active ingredients, such as expectorants (clobutinol, salbutamol), throat disinfectants, vitamins and/or trace elements, even in low dosage, can be incorporated into a soluble chewing gum material in an appropriately exact dose, which can be compressed, by technology meeting the pharmaceutical requirements, to give tablets which result in a soluble, chewable material.

This object is achieved for the first time in a surprising manner by the combination of the features or measures stated in claim 1, by virtue of the fact that a granular material is formed owing to the composition and the process. Further preferred embodiments of the invention are described in the features of the dependent claims. The invention proposes this novel product and preparation process, which avoids the abovementioned disadvantages and meets the desired requirements. This is achieved by the fact that the composition and the process provide a granular material, good processibility—in particular during comminution and admixing of further additives and with regard to the compressibility—being possible by cooling.

In the context of the invention, "chewable components" are to be understood as meaning all those substances which, alone or mixed with one another, behave like chewing gum for at least 1, preferably at least 2, in particular at least 3, min when chewed, but begin to dissolve during this time and are then completely dissolved and swallowed with the saliva. This range of substances includes, inter alia, but not exclusively: gum arabic, tragacanth, guar gum, xanthan gum, pectins; but also dry syrups, such as, for example, dry glucose syrup and/or fructose syrup; soluble cellulose derivatives, such as, for example, sodium carboxymethylcellulose. Dry glucose syrup likewise exhibits partly rubber-like behavior on chewing.

In comparison, in the context of the invention, "syrup components" are understood as meaning exclusively those which are used either as syrup or in highly concentrated solution, such as, for example, 80% glucose syrup, 70% maltodextrin solution, swollen gelatin, but also other syrups, such as corn, sugar or invert sugar syrup (Invertin® Merck). Glucose syrup can be completely or partly replaced by other concentrated carbohydrate, sugar alcohol, gelatin or similar solutions. It is important to maintain as small an amount of water as possible, since the mixture otherwise becomes a slurry, as in the prior art. On the other hand, a certain amount of moisture, from about 4 to about 7%, must remain in the coated tablet since, on drying out and at a moisture content of less than 2%, the tablet would no longer give a malleable, chewable material and would become too hard to bite.

Fat components used may be all edible, animal and vegetable fats. These are triglycerides which essentially consist of mixtures of glyceryl esters of higher fatty acids, in particular of vegetable or animal origin, for example of the order of magnitude of $C_{10}$ to $C_{22}$, whose melting point is not below 60° C.

The addition of waxes, such as, for example, beeswax, solid paraffin, ozocerite or similar substances, which ensure a longer chewing time, have proven particularly advantageous with regard to the chewability. The addition of beeswax, in particular, improves the chewability and reduces the adhesion to the teeth. The addition of relatively small amounts of glycerol or propylene glycol makes the tablet core softer to bite.

The process is carried out in principle according to the following scheme: all powder components are introduced into a surface mixer and mixed at slow speed. Thereafter, glycerol and a melt comprising fats and waxes are introduced and carefully mixed with the powder. Finally, a—for example carbohydrate-containing—syrup is added and if required—for example for reducing the viscosity to facilitate processing—can be heated to about 40° C., but unheated glucose syrup may also be used. Mixing is continued until a crumbly mass forms. The addition of the pharmaceutical active ingredient depends on its type, i.e. on its taste and/or on its stability criteria; if it is stable and has a neutral taste, it is added simply by mixing as a powder into the starting mixture; in another case, it is added, for example, by dissolving in the fat melt, surrounded by the hydrocolloid, or in a matrix whose taste has been masked by suitable measures, for example, in the case of dimenhydrinate, in polymethacrylic esters, HPMCP (hydroxypropylmethylcellulose phthalate), alginic acid and the like.

The crumbly material can be cooled either batchwise in bags of plastics sheet, for example in a refrigerator or freezer, or during passage on a cooling conveyor belt. For example, the bags are placed in a bed of dry ice and covered with dry ice. Thereafter, the material can be comminuted to the desired particle size of from about 2 to about 5 mm—for example by milling and sieving. The additives, such as, for example, additional artificial sweeteners, flavors and the like, and active ingredients or active ingredient mixtures, active ingredient matrix, etc., are then mixed with this comminuted material. The final mixture is then fed—expediently via a cooling zone, for example through a double jacket which is cooled on the outside with brine coolant—to a tablet press, preferably a rotary tablet press, and is compressed to give tablets of the desired size.

The temperature to which freezing or cooling is effected should be tailored to the respective mixture. The individual components of the mixture form a complex system with one another and mutually influence one another with respect to the behavior during the milling process and the compressibility. If the moisture content is at the upper limit, freezing must be effected to lower temperatures. Furthermore, it should be ensured that processing takes place as far as possible in a closed system and/or in a room with low atmospheric humidity and/or during short periods, in order to keep the condensation of atmospheric humidity on the material as small as possible or to take this moisture into account during formulation.

The tablets in the form of tablet cores can then be coated in a manner known per se. During coating, the cores are as a rule warmed to about 40 to about 50° C. At this temperature, the moisture which was added with concentrated syrup solution and/or gelatin solution penetrates the chewable components, and a very readily chewable material is formed, the dry syrup promoting or improving the chewability.

The product defined in claim 1 presumably has—owing to compression of the cooled granules—a particulate structure in which the moisture is initially immobilized by the low temperature. After compression, this moisture becomes mobile owing to heating (in particular during the coating process) and migrates or diffuses—initially at the surface—into the water-soluble ingredients present. These are partially dissolved and give a highly viscous, thixotropic, chewable material.

The invention is illustrated in more detail below by the Examples.

EXAMPLES 1 to 8

First, the variability of the individual components is described. The various compositions are compared with one another in Table 1.

In Examples 1 to 3, the waxes are varied: 1. paraffin, 2. ozocerite, 3. beeswax.

In Examples 2 to 4, the fat or wax components are varied: coconut oil and vegetable and animal triglycerides.

In Examples 5 to 8, various chewable components and—associated therewith—also various carbohydrate-containing syrups and swollen gelatin or, in Example 7, a sugar alcohol are used.

The preparation of the mixtures according to the invention in these Examples is carried out as follows:

For Examples 1 to 4, the spray-dried gum arabic rice starch, dry glucose syrup and aspartame are introduced into a surface mixer and mixed at slow speed. Thereafter, glycerol is introduced and distributed, and finally the mixture, melted at about 40° C., of coconut oil with paraffin or ozocerite (Examples 1 and 2) or the melt of margarine or animal fat, in each case with beeswax (Examples 3 and 4), is applied and mixed in. Finally, the liquid glucose syrup is stirred in. After careful mixing for 5 min, the material is frozen at about −12° C., then milled to 2.0 to 3.5 mm, cooled and finally compressed to give tablets, which are then coated.

For Examples 5 and 6, an analogous procedure is carried out except that tragacanth is used (Example 5) instead of spray-dried gum arabic, and in Example 6 the 80% glucose syrup is replaced by a 70% maltodextrin solution and maltodextrin powder is also used. For Examples 7 and 8, the gelatin is first allowed to swell in the citric acid/water solution; mannitol or lactose is then stirred in. The material obtained is introduced into a mixing vessel which already contains premixed spray-dried gum arabic, rice starch and aspartame. Glycerol, the coconut oil/beeswax melt and the glucose syrup are then introduced and distributed in an analogous manner. The material is then frozen, milled, cooled again and compressed.

TABLE 1

| Example No. | 1 | 2 | 3 | 4 | 5 | 6 | 7 | 8 |
|---|---|---|---|---|---|---|---|---|
| Gum arabic | 18.14 | 18.14 | 18.14 | 18.14 | | 18.14 | 18.14 | 18.14 |
| Glycerol | 0.31 | 0.31 | 0.31 | 0.31 | 0.31 | 0.31 | 0.31 | 0.31 |
| Rice starch | 8.32 | 8.32 | 8.32 | 8.32 | 8.32 | 8.32 | 8.32 | 8.32 |
| Glucose syrup (dried) | 27.20 | 27.20 | 27.20 | 27.20 | 27.20 | 27.20 | | |
| Beeswax | | | 0.67 | 0.67 | 0.67 | 0.67 | 0.67 | 0.67 |
| Coconut oil | 6.13 | 6.13 | | | 6.13 | 6.13 | 6.13 | 6.13 |
| Glucose syrup (liquid) | 39.04 | 39.04 | 39.04 | 39.04 | 39.04 | | 39.04 | 39.04 |
| Aspartame | 0.19 | 0.19 | 0.19 | 0.19 | 0.19 | 0.19 | 0.19 | 0.19 |
| Paraffin | 0.67 | | | | | | | |
| Ozocerite | | 0.67 | | | | | | |
| Margarine | | | 6.13 | | | | | |
| Animal fat | | | | 6.13 | | | | |
| Tragacanth | | | | | 18.14 | | | |
| Maltodextrin (powder) | | | | | | 18.85 | | |
| Maltodextrin (70% solution) | | | | | | 20.19 | | |
| Mannitol | | | | | | | 25.07 | |
| Citric acid | | | | | | | 0.11 | 0.20 |
| Water | | | | | | | 0.86 | 1.70 |
| Gelatin | | | | | | | 1.16 | 2.27 |

TABLE 1-continued

| Example No. | 1 | 2 | 3 | 4 | 5 | 6 | 7 | 8 |
|---|---|---|---|---|---|---|---|---|
| Lactose | | | | | | | | 23.03 |
| | 100.00 | 100.00 | 100.00 | 100.00 | 100.00 | 100.00 | 100.00 | 100.00 |

TABLE 2

| Example No. | Chewability | Chewing time |
|---|---|---|
| 1 | Not crumbly, chewable, malleable | 110–120 sec |
| 2 | Not crumbly, chewable, malleable | 105–125 sec |
| 3 | Not crumbly, chewable, malleable | 110–120 sec |
| 4 | Not crumbly, chewable, malleable | 95–100 sec |
| 5 | Not crumbly, readily chewable | 100–110 sec |
| 6 | Not crumbly, readily chewable, good taste | 105–115 sec |
| 7 | Not crumbly, readily chewable, malleable | 35–40 sec |
| 8 | Not crumbly, pleasant disintegration behavior | 30–35 sec |

The results of Examples 1 to 8 are shown in Table 2, it being evident that the chewing time is reduced when mannitol and lactose are used.

EXAMPLES 9 TO 12

The Examples describe various possible combinations and their amounts of chewable components, of fats and waxes and of carbohydrate-containing syrups.

The compositions are shown in Table 3. The preparation is carried out analogously to the abovementioned Examples. The results are shown in Table 4. For Example 12, the preparation process is to be described again in detail below (all amounts in percent by weight):

18.1% of spray-dried gum arabic, 27.1% of dry glucose syrup, 8.3% of rice starch and 0.3% of aspartame are mixed in a surface mixer for 5 min, 0.3% of glycerol is then added and mixing is carried out at a medium stirring speed of 1 to 2 min. Thereafter, a liquid fat melt heated to 40° C. and comprising 6.1% of hydrogenated coconut fat, 0.7% of beeswax and 0.2% of peppermint oil is introduced and distributed for 3 min in the mixture. Thereafter, 39.0% of 80% glucose syrup are introduced with continuous stirring and distributed uniformly for 5 min. The resulting, crumbly material is frozen and is milled in an attrition mill to 3.5 mm particle size. The granules obtained are cooled again to 0 to −10° C. and compressed at 0° C. to give tablets, which are then coated.

TABLE 3

| Example No. | 9 | 10 | 11 | 12 |
|---|---|---|---|---|
| Gum arabic (Spraygum) | 55.20 | 43.19 | 29.13 | 18.15 |
| Rice starch | | | 3.78 | 8.33 |
| Glucose syrup, dried | | | 29.13 | 27.20 |
| Beeswax | | | | 0.67 |
| Coconut oil, hydrogenated | 5.53 | 4.29 | 2.91 | 6.13 |
| Glucose syrup, liquid | 38.68 | 42.92 | 34.65 | 39.00 |
| Peppermint oil | 0.19 | 0.19 | 0.11 | 0.19 |
| Aspartame | 0.40 | 0.33 | 0.29 | 0.33 |
| Citric acid powder | | | 0.43 | |
| Gelatin | | | 8.65 | |
| | 100.00 | 100.00 | 100.00 | 100.00 |

TABLE 4

| Example No. | Chewability | Chewing time | Compression temperature |
|---|---|---|---|
| 9 | Not crumbly, pleasant disintegration behavior | 80–85 sec | minus 15° C. |
| 10 | Not crumbly, pleasant disintegration behavior | 100–110 sec | minus 11° C. |
| 11 | Not crumbly, pleasant disintegration behavior | 100 sec–110 sec | minus 8° C. |
| 12 | Not crumbly, pleasant disintegration behavior | 120 sec–130 sec | minus 5° C. |

EXAMPLES 13 TO 16 (NEGATIVE EXAMPLES, SEE TABLE 5)

The composition according to Example 13 is prepared by a procedure in which first sugar and citric acid are dissolved in water, gelatin is added and allowed to swell and then Invertin is added. The gum arabic is then introduced, and the fat is melted and worked in. Thereafter, first tylose and carboxymethylcellulose and then the cyclodextrin are added. Thereafter, ozocerite, beeswax and paraffin are melted and are mixed with the previously obtained material. Freezing, milling and compression are then carried out.

Owing to a very pronounced adhesive property, the product is difficult to compress, which is likely to be due on the one hand to the absence of a fat or wax component, such as coconut oil, and on the other hand to the sugar solution and carboxymethylcellulose, which absorbs a relatively large amount of moisture and therefore sticks to a greater extent under the compression pressure so that, so to speak, no water film or fat film can form, which film serves as a lubricant during compression.

In Example 14, the procedure is as in Example 13 except that Witepsol® is added instead of paraffin. The material can be compressed but the end product has a relatively short chewing time and disintegrates too rapidly, which is likely to be due to Witepsol® which, owing to its melting point (32° C.), melts away very rapidly in the mouth and thus prevents the formation of a cohesively chewable material during chewing.

TABLE 5

| Example No. | 13 | 14 | 15 | 16 |
|---|---|---|---|---|
| Sugar | 24.34 | 19.15 | 28.85 | |
| Water | 4.80 | 3.74 | 7.27 | |
| Invertin | 0.36 | 0.28 | | |
| Gelatin | 3.54 | 2.77 | 6.61 | |
| Galafett 36 | 0.72 | 0.58 | | |
| Gum arabic | 8.00 | 6.28 | 9.61 | 79.92 |
| Tylose C 10 000 P | 1.44 | 1.13 | | |
| Cyclodextrin | 21.57 | 16.92 | | |
| Citri cacid | 0.01 | 0.01 | 0.58 | |
| Paraffin | 7.69 | | | |
| Ozocerite | 13.07 | 20.55 | | |
| Beeswax | 8.46 | 13.23 | | |
| Carboxymethylcellulose 7HXF | 5.00 | | | |
| Peppermint flavour | 1.00 | | 1.00 | |

TABLE 5-continued

| Example No. | 13 | 14 | 15 | 16 |
|---|---|---|---|---|
| Witepsol H32 | | 15.38 | | |
| Coconut oil, hydrogenated | | | 6.00 | 7.69 |
| Corn starch | | | 3.50 | |
| Maltodextrin | | | 28.85 | |
| Glucose syrup, liquid | | | 7.23 | 15.39 |
| Aerosil | | | 0.50 | |
| | 100.00 | 100.00 | 100.00 | 100.00 |
| Note: | Cannot be compressed | Disintegrates too rapidly on chewing | Crumbly | |

The mixture according to Example 15 is prepared by a procedure in which the gelatin is first allowed to swell and is then mixed with the glucose syrup. The solids are mixed in a surface mixer; the molten coconut fat is then mixed in and finally the gelatin/glucose syrup material is added. The entire material is then heated to 80° C., whereupon it becomes pasty, and is then frozen, mixed with Aerosil and milled. Flavor is then mixed in and the material is cooled again prior to compression. 20 parts of glucose syrup are then added and are thoroughly distributed while stirring.

The material remains crumbly, which is likely to be due to the evaporation of the water as a result of heating to 80° C. Moreover, this heating promotes the migration of moisture into the solids, which is held in the powder particles, preferably in substances such as corn starch and maltodextrin, which, for example, can absorb 5 to 7% of water in addition to their own initial water content of 5 to 7% without losing their pulverulent structure. After compression with warming, such as, for example, during tablet coating, this moisture is then no longer available for achieving the desired effect of a chewable material.

For Example 16, 10 parts of molten, hydrogenated coconut oil are added to 100 parts of spray-dried gum arabic at room temperature and thoroughly stirred. 20 parts of glucose syrup are then added and are thoroughly distributed with stirring. The very large amount of gum arabic results in an excessively strong adhesion effect on the teeth, an excessively short chewing time and a rather too sticky feeling when chewing in the mouth.

EXAMPLES 17 TO 23 (WITH ACTIVE INGREDIENTS)

A very wide range of active ingredient groups can be used, buccally absorbable active ingredients and active ingredients which are effective in the oropharyngeal cavity, such as oral and throat disinfectants, being particularly suitable. Vitamins and minerals, expectorant and mucolytic substances, as well as antiemetics and antiallergics, can furthermore be administered in this form. The compositions are shown in Table 6, the preparation is carried out analogously to Examples 1 to 12, and the results are reproduced in Table 7.

In Examples 17 to 20, dimenhydrinate is used as the active ingredient in a matrix whose taste is masked; in Examples 21 to 23, a commercial 50% vitamin E powder is used.

The active ingredient matrix for Example 17 is prepared by a procedure in which 60 parts by weight of dimenhydrinate are dissolved in 40 parts by weight of ethanol, 4 parts by weight of sodium bicarbonate are then suspended in the active ingredient solution and a solution of 36 parts by weight of Eudragit S 100 in 144 parts by weight of ethanol is added. After mixing, the solvent is evaporated and the residue is vacuum-dried and is sieved to 0.8 mm.

TABLE 6

| Example No. | 17 | 18 | 19 | 20 | 21 | 22 | 23 |
|---|---|---|---|---|---|---|---|
| Gum arabic | 18.11 | 17.86 | 42.47 | 27.13 | 12.01 | 12.01 | 12.01 |
| Glycerol | 0.31 | 0.31 | | | 0.27 | 0.27 | 0.27 |
| Rice starch | 2.76 | 2.09 | | 3.48 | 5.51 | 5.51 | 5.51 |
| Glucose syrup, dried | 27.09 | 26.67 | | 27.13 | 17.97 | 17.91 | 17.97 |
| Beeswax | 0.67 | 0.67 | | | 0.59 | 1.67 | 2.75 |
| Coconut oil, hydrogenated | 6.11 | 6.00 | 4.23 | 4.07 | 5.41 | 4.32 | 3.24 |
| Glucose syrup, liquid | 38.88 | 38.33 | 42.27 | 33.33 | 34.38 | 34.38 | 34.38 |
| Peppermint oil | 0.19 | 0.19 | 0.19 | 0.19 | | | |
| Aspartame | 0.33 | 0.33 | 0.33 | 0.33 | 0.29 | 0.29 | 0.29 |
| Calcium carbonate | | 1.33 | | | | | |
| Active ingredient matrix | 5.55 | 6.22 | 4.00 | 4.33 | 23.58 | 23.58 | 23.58 |
| Citric acid powder | | | | 0.42 | | | |
| Gelatin | | | | 6.29 | | | |
| | 100.00 | 100.00 | 100.00 | 100.00 | 100.00 | 100.00 | 100.00 |

TABLE 7

| Example No. | Chewability | Chewing time |
|---|---|---|
| 17 | Not crumbly, pleasant chewing behavior | 90–100 sec |
| 18 | Good taste Readily chewable, malleable | 110–120 sec |
| 19 | Malleable | 100–110 sec |
| 20 | Pleasant disintegration behavior | 95–105 sec |
| 21 | Good chewing behavior, malleable | 110–120 sec |
| 22 | Readily chewable | 90–100 sec |
| 23 | Readily chewable, pleasant disintegration behavior | 110–120 sec |

An analogous procedure is used for Example 18, except that 53.6 parts by weight of dimenhydrinate are dissolved in 40.2 parts by weight of ethanol; 3.5 parts by weight of sodium bicarbonate and 10.7 parts by weight of calcium carbonate are then suspended in the solution. Thereafter, a solution of 32.2 parts by weight of Eudragit S 100 in 128.7 parts by weight of ethanol is admixed, and the procedure is otherwise as in Example 17.

For Example 19, after the addition of citric acid, the gelatin is allowed to swell in the glucose syrup at elevated temperature for one hour and is not dissolved, in order to avoid introducing too much water. This mixture is stirred into the gum arabic to which the molten coconut fat had been added, and is cooled, milled, cooled again and finally compressed analogously to the preceding Examples.

EXAMPLES 24 TO 29 (FOR COMPOSITIONS, CF. TABLE 8)

| Example No. | 24 | 25 | 26 | 27 | 28 | 29 |
|---|---|---|---|---|---|---|
| Gum arabic | 16.50 | 16.50 | 16.50 | 16.50 | 16.50 | 16.50 |
| Glycerol | 0.30 | 0.30 | 0.30 | 0.30 | 0.30 | 0.30 |
| Rice starch | 7.80 | 3.60 | 7.80 | 7.80 | 1.50 | 3.40 |
| Dried glucose syrup | 25.00 | 25.00 | 25.00 | 25.00 | 25.00 | 25.00 |
| Beeswax | 0.95 | 0.95 | 0.95 | 0.95 | 0.95 | 0.95 |
| Coconut oil, hydrogenated | 5.60 | 5.60 | 5.60 | 5.60 | 5.60 | 5.60 |
| Glucose syrup, liquid | 35.95 | 35.95 | 35.95 | 35.95 | 35.95 | 35.95 |
| Aspartame | 0.30 | 0.30 | 0.30 | 0.30 | 0.30 | 0.30 |
| Haltrin M700 | 7.475 | 4.175 | 3.81 | 2.79 | 0.77 | 3.06 |
| Salbutamol sulfate | 0.125 | | | | | |
| Vitamin mixture (*) | | 7.625 | | | | |
| Trace element mixture (**) | | | 3.789 | | | |
| Cetylpyridinium chloride matrix | | | | 4.81 | | |
| Zinc matrix | | | | | 13.13 | |
| Acetylcysteine matrix | | | | | | 8.94 |
| | 100.00 | 100.00 | 100.00 | 100.00 | 100.00 | 100.00 |

(*) Allowable daily dose per tablet (mg):
Thiamine nitrate (vitamin B1) 2.073
Riboflavin-5'-phosphate sodium (vitamin B2) 2.584
Nicotinamide 21.000
Calcium D-pantothenate 6.848
Pyridoxine hydrochloride (vitamin B6) 2.680
Cyanocobalamin 0.1% (vitamin B12) 3.150
Folic acid 0.185
Biotin 0.032
Mannitol 6.448
(**) Trace element mixture in the following composition:
0.029% of chromium orotate = 40 mcg of Cr per tablet
1.613% of manganese orotate = 3.3 mg of Mn per tablet
0.008% of potassium iodide = 0.1 mg of I per tablet
2.139% of zinc acetate hydrate = 10.0 mg of Zn per tablet
3.789%

In these Examples, various active ingredients are added to a constant composition. The coated tablets prepared analogously to Examples 17 to 23 with spray-dried gum arabic. (Spraygum) all have good chewing behavior and a pleasant taste. A soluble coated chewable tablet containing multivitamins can also be prepared, the vitamins preferably being used in the corresponding daily allowance (cf. Example 25).

The active ingredients of Examples 27 to 29 are introduced in the form of a matrix which is known per se and whose taste has been masked. The dose is as follows: in Example 27, 2 mg of cetylpyridinium chloride per tablet; in Example 28: 25 mg of zinc per tablet; and in Example 29: 100 mg of acetylcysteine per tablet.

The following active ingredients are further Examples of the expedient application of the invention: cardiovascular drugs, such as, for example, salbutamol; mucolytics and expectorants, it being necessary to incorporate the antitussive clobutinol into a matrix, owing to the bitter taste; antihistamines, such as cetirizine and loratadine; oropharyngeal therapeutic drugs, such as cetylpyridinium chloride, benzalkonium chloride, dequalinium chloride, which are preferably likewise present in the form of an active ingredient matrix, it also being possible to prepare a fat and wax matrix.

EXAMPLE 30
With Diclofenac Sodium or Diclofenac Potassium as Active Ingredient
Preparation of the Coated Chewable Tablets:
5 parts by weight of aspartame, 637 parts by weight of solid glucose syrup, 194 parts by weight of spray-dried gum arabic and 74 parts by weight of maltodextrin (Maltrin M700) are homogeneously mixed in a mixer. Thereafter, 28 parts by weight of propylene glycol are homogeneously distributed and a melt of 74 parts by weight of coconut fat, 13 parts by weight of beeswax and 3 parts by weight of peppermint oil is then applied and is uniformly distributed while stirring. Thereafter, a hot solution consisting of 315 parts by weight of liquid glucose syrup and 88.5 parts by weight of sorbitol is stirred in. 70 parts by weight of dextrin and 37 parts by weight of hydrogenated castor oil are then added, followed, after cooling, by 1.6 parts by weight of magnesium stearate. A Eudragit matrix of diclofenac sodium, corresponding to 12.5 mg of diclofenac sodium or corresponding to 25 mg of diclofenac sodium, is mixed with the material sieved to 2 mm after cooling, and the mixture is compressed to give 1.6 g cores.

Both diclofenac sodium and diclofenac potassium can be used in the appropriate amount.

We claim:
1. A soluble chewable tablet comprising
   a pharmaceutically active ingredient, whereby said pharmaceutically active ingredient is slowly released when said tablet is chewed, said tablet becoming thixotropic when chewed but not fully dissolving for at least one minute when chewed, and said tablet slowly dissolves when said tablet is chewed after said at least one minute, so as to completely dissolve thereafter in saliva during chewing;
   10 to 60 percent by weight of at least one chewable component selected from the group consisting of gum arabic, tragacanth, guar gum, dry glucose syrup, dry fructose syrup and carboxymethyl cellulose:

20 to 50 percent by weight of at least one syrup component selected from the group consisting of carbohydrate syrup, concentrated maltodextrin solution and sugar alcohol syrup;

2 to 12 percent by weight of at least one fat or wax component selected from the group consisting of fat components having a melting point not above 60° C. and wax components having a melting point of less than 70° C.; wherein the chewable component is partially dissolved by the syrup component.

2. The tablet according to claim 1, comprising 20 to 50 percent by weight of chewable components.

3. The tablet according to claim 1, comprising 25 to 45 percent by weight of syrup components.

4. The tablet according to claim 1, comprising 4 to 8 percent by weight of fat or wax components.

5. The tablet according to claim 1, additionally comprising 5 to 40 percent by weight of at least one filler.

6. The tablet according to claim 5, comprising 15 to 30 percent by weight of at least one filler.

7. The tablet according to claim 1, additionally comprising at least one component of the group of 0.1 to 3 percent by weight of glycerol, 0.1 to 3 percent by weight of propylene glycol and 1 to 10 percent by weight of swollen gelatin.

8. The tablet according to claim 7, comprising at least one component of the group of 0.2 to 0.5 percent by weight of glycerol, 0.2 to 0.5 percent by weight of propylene glycol and 2 to 8 percent by weight of swollen gelatin.

9. The tablet according to claim 1, wherein the syrup component is selected from the group consisting of glucose syrup, fructose syrup, invert sugar, sucrose syrup, corn syrup, maltodextrin solution and sorbitol syrup.

10. The tablet according to claim 5, wherein the filler is selected from the group consisting of hydrolyzed starch, maltodextrin, sugars and sugar alcohols.

11. The tablet according to claim 1, wherein the fat or wax component is selected from the group consisting of triglycerides, glyceryl esters of fatty acids, beeswax, paraffin and ozocerite.

12. The tablet according to claim 11, wherein the fat or wax component is selected from the group consisting of vegetable and animal fat of the order of $C_{10}$ to $C_{22}$.

13. The tablet according to claim 1, wherein the at least one fat or wax component melts at above 34° C.

14. The tablet according to claim 13, wherein the at least one fat or wax component melts at about 45° C.

15. The tablet according to claim 1, additionally comprising 0.1 to 30 percent by weight of a pharmaceutically active ingredient.

16. The tablet according to claim 15, wherein the pharmaceutically active ingredient is embedded in a matrix.

17. The tablet according to claim 15, wherein the pharmaceutically active ingredient is selected from the group consisting of antiemetics, vitamin E, cardiovascular drugs, mucolytias, expectorants antihistamines and oropharyngeal therapeutic drugs.

18. The tablet according to claim 17, wherein the pharmaceutically active ingredient is selected from the group consisting of dimenhydrinate, salbutamol, clobutinol, cetirizine, loratidine, cetylpyridinium chloride, benzalkonium chloride and dequalinium chloride.

19. The tablet according to claim 18, which contains 0.5 to 5% by weight of dimenhydrinate;

30 to 45% by weight of glucose syrup;

20 to 30% by weight of dry glucose syrup;

4 to 8% by weight of hydrogenated coconut oil;

0.5 to 2.0% by weight of beeswax;

1 to 8% by weight of rice starch;

12 to 25% by weight of gum arabic; and 4 to 10% by weight of maltodextrin.

20. The tablet according to claim 19, wherein the tablet additionally contains an active ingredient matrix and 1 part by weight of dimenhydrinate is embedded in 0.5 to 2 parts by weight of the active ingredient matrix, said matrix comprising 25 to 40% by weight of at least one polymetacrylic acid ester.

21. A process for the production of a soluble chewable tablet, containing a pharmaceutically active ingredient and at least one chewable component selected from the group consisting of:

gum arabic, tragacanth, guar gum, dry glucose syrup, dry fructose syrup, and soluble carboxymethyl cellulose derivative;

at least on syrup component selected from the group consisting of:

carbohydrate syrup, concentrated maltodextrin solution, and sugar alcohol syrup; and at least one fat or wax component selected from the group consisting of: fat components having a melting point not above 60 degrees C., and wax components having a melting point of less than 70 degrees C.;

wherein the pharmaceutically active ingredient and said components are mixed together, and wherein pulverulent chewable components are mixed with the molten fat or wax components, after which, with the addition of at least one syrup component, the mixture then becomes a crumbly material, which in a first cooling step is cooled to below 0 degrees C., then milled to a particle size of not more than 5 mm and, after a second cooling step to below 10 degrees C. is compresses to give tablets, whereby said pharmaceutically active ingredient is slowly released when said tablets are chewed, said tablets becoming thixotropic when chewed but not fully dissolving for at least one minute when chewed, and said tablets slowly dissolve when said tablets are chewed after said at least one minute, so as to completely dissolve thereafter in saliva during chewing.

22. The process according to claim 21, wherein the first cooling step brings the mixture to below −10° C. and/or the second cooling steps brings the mixture to below 0° C.

23. The tablet according to claim 1, which is chewable for at least 90 seconds, before it is dissolved and sucked with the saliva.

24. A soluble chewable table comprising a pharmaceutically active ingredient and at least one chewable component selected from the group consisting of:

gum arabic, tragacanth, guar gum, dry glucose syrup, dry fructose syrup, and carboxymethyl cellulose;

at least one syrup component selected from the group consisting of:

carbohydrate syrup, concentrated maltodextrin solution, and sugar alcohol syrup; and at least one fat or wax component selected from the group consisting of:

fat components having a melting point not above 60 degrees C., and wax components having a melting point of less than 70 degrees C.;

obtainable by a process wherein the pulverulent chewable components are mixed with the molten fat or wax components, after which, with the addition of said syrup component, the mixture then becomes a crumbly material, which in a first cooling step is cooled below 0 degrees C., then milled to a particle size of not more than 5 mm and, after a second cooling step below 10 degrees C. is compressed to give tablets, whereby said pharmaceutically active ingredient is slowly released when said tablets are chewed, said tablets becoming thixotropic when chewed but not fully dissolving for at least one minute when chewed, and said tablets slowly dissolve when said tablets are chewed after said at least one minute, so as to completely dissolve thereafter in saliva during chewing.

25. The tablet according to claim 22, which contains 10 to 60 percent by weight of at least one chewable component;

20 to 50 percent by weight of at least one syrup component; and 2 to 12 percent by weight of at least one fat or wax component.

26. A method of administering a pharmaceutically active ingredient to a patient, comprising:

a) providing a soluble chewable tablet as set forth in claim 1;

b) slowly releasing said active ingredient to the patient by having the patient chew said tablet such that said tablet becomes thixotropic when chewed but does not dissolve for at least one minute when chewed.

27. The method of claim 26, further including having said tablet slowly dissolve when said tablet is chewed after said at least one minute, so as to completely dissolve thereafter in saliva during chewing.

28. A method of administering a pharmaceutically active ingredient to a patient, comprising:

a) providing a soluble chewable tablet produced by the process for the production of a soluble chewable tablet as set forth in claim 21;

b) slowly releasing said active ingredient to the patient by having the patient chew said tablet such that said tablet becomes thixotropic when chewed but does not dissolve for at least one minute when chewed.

29. The method of claim 28, further including having said tablet slowly dissolve when said tablet is chewed after said at least one minute, so as to completely dissolve thereafter in saliva during chewing.

30. A method of administering a pharmaceutically active ingredient to a patient, comprising:

a) providing a soluble chewable tablet as set forth in claim 24;

b) slowly releasing said active ingredient to the patient by having the patient chew said tablet such that said tablet becomes thixotropic when chewed but does not dissolve for at least one minute when chewed.

31. The method of claim 30, further including having said tablet slowly dissolve when said tablet is chewed after said at least one minute, so as to completely dissolve thereafter in saliva during chewing.

* * * * *